US012606474B2

(12) United States Patent
Yu et al.

(10) Patent No.: US 12,606,474 B2
(45) Date of Patent: Apr. 21, 2026

(54) METHOD FOR REMOVING TBBPA IN WATER, MICROBIAL STRAIN AND MICROBIAL AGENT

(71) Applicant: South China Institute of Environmental Science, Ministry of Ecology and Environment, Guangzhou (CN)

(72) Inventors: Yunjiang Yu, Guangzhou (CN); Haobo Guo, Guangzhou (CN); Zhaofeng Chang, Guangzhou (CN); Xiaohui Zhu, Guangzhou (CN); Zijuan Zhong, Guangzhou (CN); Zhenchi Li, Guangzhou (CN); Mingdeng Xiang, Guangzhou (CN)

(73) Assignee: South China Institute of Environmental Science, Ministry of Ecology and Environment, Guangzhou (CN)

( * ) Notice: Subject to any disclaimer, the term of this patent is extended or adjusted under 35 U.S.C. 154(b) by 620 days.

(21) Appl. No.: 17/959,307

(22) Filed: Oct. 4, 2022

(65) Prior Publication Data

US 2023/0040809 A1 Feb. 9, 2023

(30) Foreign Application Priority Data

Jan. 12, 2022 (CN) .......................... 202210029345.4

(51) Int. Cl.
| | |
|---|---|
| *C02F 3/34* | (2023.01) |
| *C02F 3/02* | (2023.01) |
| *C02F 101/34* | (2006.01) |
| *C12N 1/20* | (2006.01) |
| *C12N 1/205* | (2026.01) |
| *C12N 11/02* | (2006.01) |
| *C12R 1/01* | (2006.01) |
| *C02F 3/00* | (2023.01) |

(52) U.S. Cl.
CPC ................ *C02F 3/348* (2013.01); *C02F 3/02* (2013.01); *C12N 1/205* (2021.05); *C12N 11/02* (2013.01); *C02F 2003/003* (2013.01); *C02F 2101/345* (2013.01); *C02F 2305/06* (2013.01); *C12R 2001/01* (2021.05)

(58) Field of Classification Search
CPC ...... C02F 3/348; C02F 3/02; C02F 2003/003; C02F 2101/345; C02F 2305/06; C02F 2101/36; C02F 2209/06; C12N 1/205; C12N 11/02; C12N 1/20; C12N 1/36; C12N 11/14; C12R 2001/01; Y02W 10/10
See application file for complete search history.

(56) References Cited

U.S. PATENT DOCUMENTS

| | | | |
|---|---|---|---|
| 2004/0137002 A1 | 7/2004 | Filutowicz |
| 2019/0320661 A1 | 10/2019 | Arias et al. |
| 2019/0320662 A1 | 10/2019 | Ferreira et al. |

FOREIGN PATENT DOCUMENTS

| | | | | |
|---|---|---|---|---|
| CN | 106479931 A | * | 3/2017 | |
| FR | 3055338 A1 | * | 3/2018 | ........... C12Q 1/6806 |

OTHER PUBLICATIONS

English translation of Li, Na, CN106479931A, Espacenet. (Year: 2017).*
English translation of Cyrielle et al., FR3055338, WIPO. (Year: 2018).*
CNIPA, Notification of First Office Action for Chinese application CN202210029345.4, Jun. 22, 2022.
CNIPA, Notification to grant patent right for Chinese application CN202210029345.4, Jul. 26, 2022.

* cited by examiner

*Primary Examiner* — Robert B Mondesi
*Assistant Examiner* — Naghmeh Nina Moazzami
(74) *Attorney, Agent, or Firm* — Hemisphere Law, PLLC

(57) ABSTRACT

The present disclosure discloses a method for removing TBBPA in water, a microbial strain and a microbial agent, wherein the microbial strain is a domesticated *Burkholderia cepacia* strain, which is named Y17 with a conservation number GDMCC No. 62153. The microbial agent and the method for removing TBBPA in water with the microbial agent are that Y17 strains are colonized on the surface and pore channels of biochar, TBBPA in water is used as a carbon source, air and dissolved oxygen are used as oxygen sources, biochar provides the strains a growth microenvironment for degrading TBBPA in water, the strains are subjected to aerobic growth in water, and bio-enhanced degradation of TBBPA in water is performed by continuously degradation reaction. The removal method and the microbial strain as well as the microbial agent are high in degradation efficiency, environmental-friendly and low in cost, and can meet requirements on large-range promotion and application.

1 Claim, 10 Drawing Sheets

METHOD FOR REMOVING TBBPA IN WATER, MICROBIAL STRAIN AND MICROBIAL AGENT

TECHNICAL FIELD

The present disclosure belongs to the technical fields of microbial wastewater treatment and environmental protection, and particularly relates to a method for removing TBBPA in water, a microbial strain and a microbial agent.

BACKGROUND ART

Tetrabromobisphenol A (TBBPA) is a grey white powder, which has a melting point of 184° C. and a boiling point of 316° C. (decomposition), can be dissolved into methanol, ethanol and acetone as well as a sodium hydroxide aqueous solution, but is slightly dissolved into water, and is prone to enrichment in organisms due to its characteristics of low aqueous solubility (0.72 mg·L$^{-1}$) and high fat solubility (1 gKow=4.5). TBBPA, as a fire retardant, is ordinarily used for manufacturing circuit boards and plastics, which is necessarily released to environments in the use process of a product to harm ecology and human health. At present, it has been found that there are TBBPA in natural water (especially wastewater treatment factory, etc.) and underwater surface sediments.

In recent years, studies on technologies for treating organic pollutants in environments have been rapidly developed, which propose various pollutant environmental remediation technologies. At present, pollutant environmental remediation can be conducted by using a physical method, a chemical method and a biological method. Compared with physical remediation and chemical remediation, bioremediation has the following obvious advantages: (1) it has significantly reduced remediation cost; (2) it can be carried out on site at a pollution point, with little disturbance to environments; (3) the remediation technology itself is environmental-friendly and does not easily cause secondary pollution; and (4) it can be used for large-range pollution places. It is based on the above advantages that bioremediation has been favored by more and more environmental researchers in the past two decades, and becomes a promising method for polluted environmental remediation. However, compared with conventional remediation methods, it has its own drawbacks: (1) it has long remediation time, and is not suitable for small-range serious pollution caused by sudden accidents; (2) its remediation effect is not as complete as those of chemical remediation and physical remediation; and (3) it is significantly affected by environment factors, and its remediation conditions are not easy to manually control.

Bioremediation is a technology in which microorganisms are used to degrade toxic and harmful pollutants so as to purify water and soils. Bioremediation includes biological stimulation and biological magnification which are considered as cost-effective and effective technologies because they usually avoid dredging to control costs. Bioremediation is a process of accelerating the removal of pollutants in the environment by utilizing absorption, metabolism, degradation and other functions of microorganisms on environmental pollutants. For the pollutants in the natural environment, it is generally a controlled process or a spontaneous process.

Bioremediation contains multiple limitation factors, for example, microorganisms capable of degrading pollutants slowly grow and have a low biomass, and slow transmission rate of O$_2$ in water restricts the growth rate of microorganisms degrading pollutants, and therefore bioremediation needs biological stimulation and biological magnification to improve the removal of microorganisms on pollutants. Biological stimulation refers to stimulating the potential of indigenous microorganisms to degrade pollutants or co-metabolic degradation of target pollutants through addition of appropriate electron donors/receptors or nutrients. However, these stimulative effects are established on the basis that indigenous microbial floras have the ability of degrading pollutants, thus there are many uncertainties for biological stimulation. First of all, whether the polluted water contains microorganisms capable of degrading pollutants, and the time it takes for generating enough microorganisms in the polluted water is uncertain or may be very long.

Biological magnification refers to accelerating the removal of pollutants in a polluted area or a bioreactor by introducing specific dominant floras or genetically engineered floras. However, due to restriction on degradation efficiency, practicality and other aspects, the biological magnification method is still in the discussion stage. Under experimental conditions, inoculating special microbial agents can often effectively remove target pollutants, but their performances are difficult to predict under natural conditions. Under some environmental conditions, biological magnification can successfully accelerate the removal of target pollutants. However, under some environmental conditions, the introduced special microbial agent has an extremely low survival rate, and cannot develop their biodegradation activity.

The existing research results include: aerobically degraded *Rhodococcus* sp., anaerobically degraded *ochrobactrum* sp., *Enterobacter* sp. and *Serratia* sp. have good a good degradation effect on TBBPA in polluted sludge. Whereas, no strains having good degradation effect on TBBPA in water have been found so far.

Therefore, there is a need for researching a method for degrading TBBPA in water through biological magnification with high degradation efficiency, small environment influence, stable biological remediation effect, environmental friendliness and low cost, a degradation strain and a microbial agent, in order to meet the demands of large-range low-cost promotion and application.

SUMMARY

In view of the above defects in the prior art, the objective of the present disclosure is to provide a method for removing TBBPA in water, a microbial strain and a microbial agent. By domesticating terrestrial microbial strains and preparing a specific microbial agent, a limitation that this strain cannot naturally grow in water is overcome, this microbial agent provides the strain reliable microenvironment conditions of growing in water. Through biological magnification, the removal of target pollutants is accelerated to achieve the bio-enhanced degradation of TBBPA in water, thereby meeting the demands of large-range low-cost safe and reliable water remediation.

In order to realize the above objective, the technical solution provided by the present disclosure is as follows:

Provided is a microbial strain for degrading TBBPA in water, wherein the strain is a domesticated *Burkholderia cepacia* strain which is named Y17 with a conservation number GDMCC No. 62153 and a conservation date of Dec. 21, 2021; it is deposited in Gaungdong Microbial Culture Collection Center (GDMCC), and the conservation address is 5th Floor, Building 59, No. 100, Xianlie Middle Road, Guangzhou City.

The Y17 strains are rejuvenated and expanded with a nutrient culture medium before being used to degrade TBBPA in water, which comprises the following process: the strains are added into the nutrient culture medium and then expanded for 12 h at 35° C. under the rotation speed of 160 r/min; the nutrient culture medium is obtained by adding 3 g of beef extract, 10 g of peptone and 5 g of NaCl into pure water, fixing the volume to 1000 mL and adjusting the pH to 7.2.

Provided is a microbial agent for degrading TBBPA in water, wherein the above-mentioned Y17 strains are colonized onto the surface and pore channels of biochar to form the microbial agent which provides growth conditions and a microenvironment for aerobic growth of Y17 strains in water to degrade TBBPA in water: the biochar is used as a carrier, the Y17 strains grow on the surface and pore channels of the biochar, the biochar adsorbs TBBPA in water to serve as a carbon source for growth of Y17 strains, air reserved in the pore channels of the biochar and dissolved oxygen in water are used as oxygen sources, and a high-osmotic pressure is provided on a contact surface between the biochar and water so that the degradation reaction can be continuously carried out.

The microbial agent has the following material performance parameters: an initial specific gravity is 0.35-0.36, a specific surface area is 11.7-11.9 m²/g, a micropore area is 0.23-0.24 m²/g, an outer surface area is 11.4-11.6 m²/g, and a pore volume is 0.02-0.03 m²/g; and a gravity after sufficient immersion is 0.98-0.99, and the biochar and the Y17 strains suspend in water for a long time so that the Y17 strains can aerobically grow for a long time to continuously degrade TBBPA in water.

Provided is the microbial agent for degrading TBBPA in water, which is prepared by using the following steps:

A, Preparation of Biochar BC biomass maize straws are dried in an oven at 60° C. and grinded via a 150 μm sieve, a certain amount of sieved biomass is put into a corundum boat to be placed in a tubular furnace, and the heating procedure of the tubular furnace is as follows: the room temperature is respectively raised to 300° C., 500° C. and 700° C. at 10° C./min for pyrolysis, the above pyrolysis temperatures are kept for 2 h, and each of the pyrolysis temperatures is reduced to 75° C. at 10° C./min, and then the biomass is taken out for future use, thereby correspondingly obtaining three kinds of biochar BC; and B, Preparation of Microbial Agent MBC Colonized by Immobilization of Biochar the biochar prepared under different pyrolysis conditions and a separated and purified single strain Y17 solution having a removal activity are subjected to immobilization culture at the temperatures of 25° C., 30° C. and 35° C. at the pH of 5, 6, 7, 8 and 9 at the rotation speed of 160 r/min to colonize microorganisms on the biochar so as to prepare the biochar immobilized microbial agent MBC, and then the prepared biochar immobilized microbial agent MBC is rinsed with sulfate buffer for future use.

Wherein, the step A also comprises: the biochar BC500 heated to 500° C. is added into a vibration screening machine, and forward and reverse alternating wetting pressure air is introduced into the vibration screening machine while vibration, ashes are removed, and the blocked pore channels are opened up so that the wet air is accommodated in each pore channel of biochar and the negative charges carried by biochar are reduced so as to facilitate the macroscopic adsorption of microorganisms and meanwhile the performance parameters of the previous biochar material are reached;

wherein, the step B also comprises: the biochar BC500 treated in step A is used as a carrier to undergo immobilization culture of biochar for 12 h at the immobilization culture temperature of 35° C. at the immobilization culture pH of 7 to prepare MBC 500.

Provided is a method for removing TBBPA in water, comprising the following steps:

S1: respectively preparing the microbial strain for degrading TBBPA in water and the above microbial agent MBC;

S2: measuring the concentration of TBBPA in wastewater and the degradation rate of the prepared microbial agent, and calculating the amount of the microbial agent required for degradation;

S3: adding the microbial agent into wastewater, stirring or vibrating the wastewater, or naturally flowing for 7-8 days, so that the microbial strain Y17 on the microbial agent is subjected to continuous aerobic growth so as to absorb and degrade TBBPA in wastewater; at this moment, an microenvironment for growth of Y17 strains is formed on the surface and pore channels of the biochar, dissolved oxygen in water and air reserved in the pore channels of biochar continuously provide oxygen sources for the degradation reaction process, and TBBPA adsorbed by biochar is used as a carbon source, and on an interface between biochar and water, a low osmotic pressure of water is hedged, and a high osmotic pressure is provided for Y17 strains; and the Y17 strains are subjected to aerobic growth and breeding in water for bio-enhanced degradation of TBBPA in water; and S4: measuring the concentration of TBBPA in the treated water, and repeating steps S2-S3 if the concentration fails to meet the standard, until qualified.

In the step S3, when water has a temperature of 25° C.-35° C. and a pH value of 6, the Y17 strain on the microbial agent has an optimal degradation efficiency of TBBPA.

In preferred embodiments, the step S1 is specifically as follows: the above microbial agent is prepared; the step S3 is specifically as follows: the microbial agent MBC is added into wastewater, the wastewater is stirred or vibrated, or naturally flows for 7-8 days, the gravity of the microbial agent after being sufficiently immersed is 0.98-0.99, the microbial agent and the Y17 strains suspend on wastewater for a long time, so that the Y17 strains can aerobically grow for a long time, so as to improve the adsorption and degradation efficiencies of TBBPA in water.

Compared with the prior art, the present disclosure has the advantages:

1. According to the method for removing TBBPA in water, the microbial strain and the microbial agent provided by the present disclosure, a limitation that this strain cannot naturally grow in water is overcome by domesticating terrestrial microbial strains and preparing a specific microbial agent so that this microbial agent provides the strain reliable microenvironment conditions of growing in water; through biological magnification, the removal of target pollutants is accelerated to achieve the bio-enhanced degradation of TBBPA in water, with high degradation efficiency, small influence of environment on degradation, stable bioremediation effect, environmental friendliness and low cost thereby meeting the demands of large-range low-cost safe and reliable water remediation.

2. The domesticated terrestrial strain Y17 provided by the present disclosure is domesticated in a culture medium based on TBBPA as a single carbon source, and is a strain having good degradation ability of TBBPA screened from terrestrial floras in the soil of an e-waste disassembly area, which is a terrestrial *Burkholderia cepacia* strain screened in the soil through genetic comparison and named Y17; the strains can be rapidly proliferated in the microenvironment provided by the microbial agent after being colonized on the microbial agent with biochar as the carrier and aerobically grow; furthermore, the strains can suspend in water along with the biochar of the microbial agent for a long time to enhance the degradation of TBBPA that is in water and adsorbed by biochar; the environmental adaptability, TBBPA degradation ability and stress resistance of the terrestrial strains after being domesticated are all significantly improved.

3. The dominant strain Y17 originating from soil is selected as a microorganism degrading TBBPA in water, and the microbial agent prepared by using biochar as the carrier provides microscopic conditions for its growth in water, so that the growth of the strains in water (or sediment) can be maintained for a long time. *Burkholderia cepacia* to which strain the Y17 stains belong is obligatory aerobic, its degradation of TBBPA is microbial aerobic degradation, the strain has an optimal growth temperature of 30~37° C., and a pH value of 7; after domestication, the strain has an appropriate temperature decreased to 25~35° C. and a pH value of 6, which improves the adaptability of the natural environment. *Burkholderia cepacia* involved by the present disclosure is not only found to live widely in soil and around the roots of plants, but also frequently detected in natural or artificial water environments such as lakes, rivers, drinking water, purified water and pipes. However, the survival of the microorganisms is generally limited by the lack of nutrients and low osmotic pressure in a water environment so that the microorganisms cannot grow and survive only by metabolic regulation and cell morphological changes but cannot survive for a long time in a stressed water environment (maintain activity but not grow) in an uncultivable state (VBNC). In the present disclosure, the specially prepared microbial agent provides the microenvironment to the strains, thereby overcoming the obstacle that the strain cannot grow in water. Specifically, by using the air reserved in the pore channels and gaps of biochar and dissolved oxygen in water as the oxygen sources, TBBPA in water adsorbed by biochar as the carbon source and the contact surface between the pore channels and surface of biochar with water as an attachment bed, the low osmotic pressure of hedged water is microenvironments, including high osmotic pressure, oxygen and nutrients (TBBPA), necessary for the growth of Y17 strains in water, including high osmotic pressure, oxygen and nutrients (TBBPA).

4. The microbial agent provided by the present disclosure is obtained by using a special BC500 biochar as the carrier and colonizing Y17 strains on the surface and pore channels (including pores and gaps) of biochar; by adjusting the preparation method and conditions of the biochar, the biochar can reach some parameters, namely, the initial specific gravity is 0.35~0.36, the pore volume is 0.02~0.03 cm$^2$/g, and the specific gravity after sufficient immersion is 0.98~0.99 (close to 1), so that the biochar and Y17 strains can suspend in water for a long time, and the Y17 strains can aerobically grow for a long time to continuously degrade TBBPA in water. Refer to FIG. 3, it can be seen by practical test that the microbial agent makes the Y17 strains continuously grow in the water environment with good growth conditions, and therefore the ability of the microbial agent to degrade TBBPA is significantly improved; the adopted BC500 biochar is a carbon material produced by biomass pyrolysis under high temperature and anoxic conditions, which has the advantages of large specific surface area, high pore channel rate and strong electron transfer ability, can provide good survive environment for microorganisms and meanwhile has excellent TBBPA adsorption ability, and then enhance the contact of microorganisms with pollutants to promote the degradation of pollutants.

5. According to the removal method provided by the present disclosure, through combination of the strains with the microbial agent, the shortcomings that the Y17 strain cannot grow in water, and its growth is easily affected by environmental factors and its degradation efficiency is low are overcome, and the stress resistance and degradation ability of the microbial Y17 strains are improved through domestication of Y17 combined with immobilized colonizing of strains with biochar, establishment of growth microenvironment and improvement of growth conditions.

6. The degradation method, microbial strain and microbial agent provided by the present disclosure have good degradation effect, environment friendliness, easy preparation, low cost and convenient use, and can be popularized and applied to control of organic pollutants TBBPA in water on large scale. By test and calculation, total control cost produced by using the technology of the present disclosure is only about 20% of that of chemical treatment method.

Next, the technical solution of the present disclosure will be described in detail in combination with drawings and embodiments.

DETAILED DESCRIPTION OF THE EMBODIMENTS

Example 1

Figure 1:
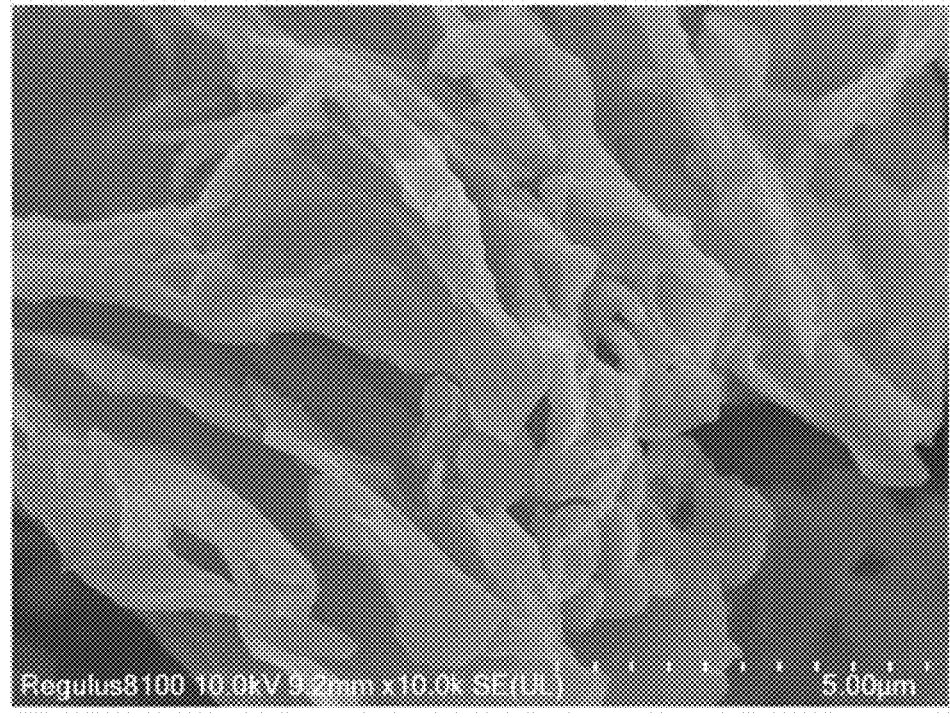
FIG. 1 is a scanning electron microscope (SEM) image of a biochar material BC500 according to embodiments of the present disclosure.
Figure 2:
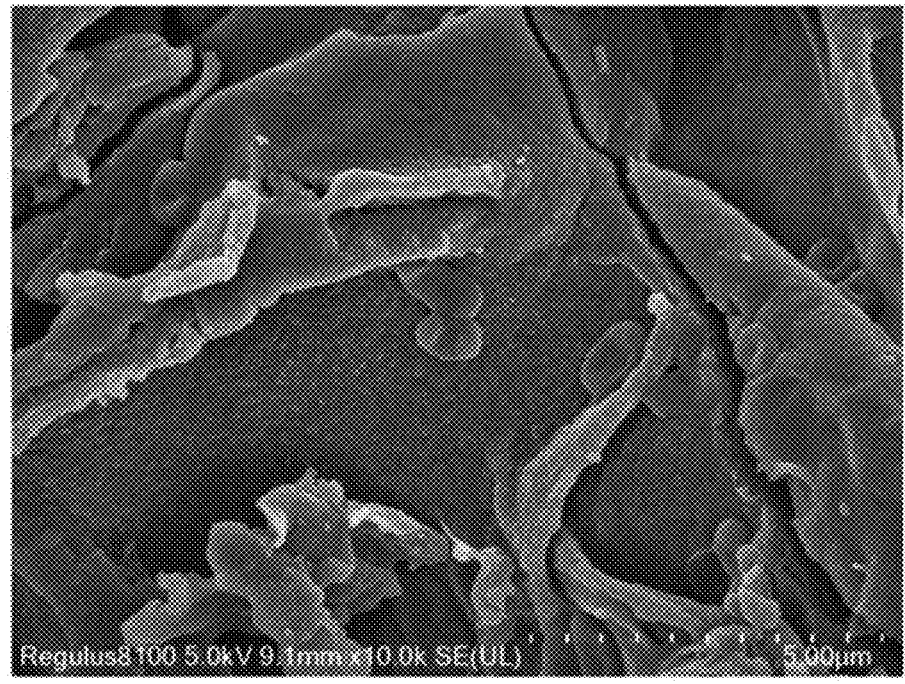
FIG. 2 is an SEM image of a microbial agent MBC500 (containing a few of strains) according to embodiments of the present disclosure.
Figure 3:
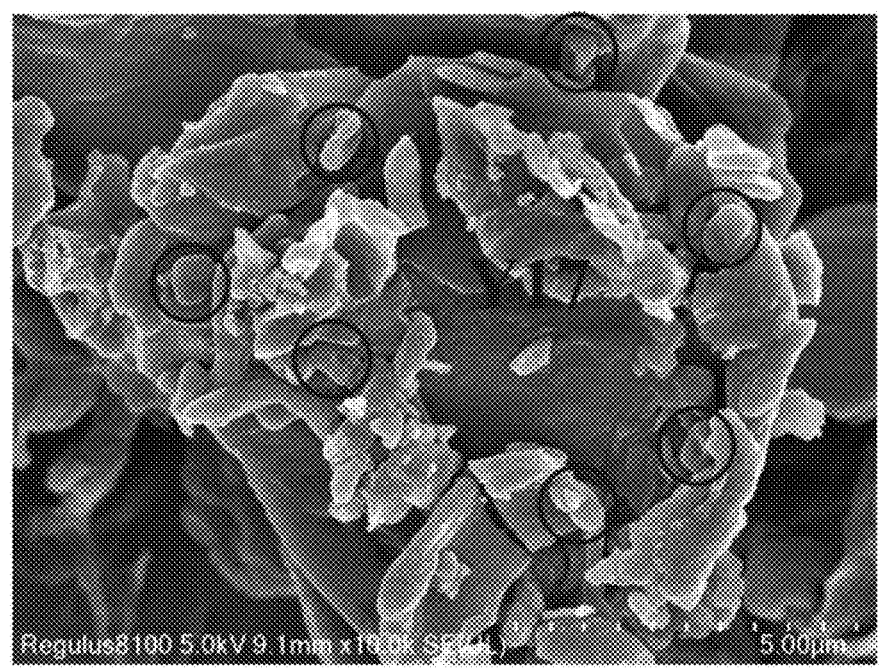
FIG. 3 is an SEM image (strains are shown in circles) of a microbial agent MBC500 according to embodiments of the present disclosure.

Refer to FIG. 1-FIG. 3, this example provides a microbial strain for degrading TBBPA in water. This strain is a domesticated *Burkholderia cepacia* strain, which is named Y17 with a conservation number GDMCC No. 62153 and deposited in Gaungdong Microbial Culture Collection Center (GDMCC) on Dec. 21, 2021, and the conservation address is 5th Floor, Building 59, Yard, No. 100, Xianlie Middle Road, Guangzhou.

This strain is domesticated in a culture medium in which TBBPA as a single carbon source, and is a terrestrial strain having a good degradation ability of TBBPA screened from the soil in an e-waste dismantling area. By gene sequencing and comparison, the strain is *Burkholderia cepacia* strain which is named Y17, and can suspend in water (a few amount of strains are precipitated in sludge) along with the microbial agent after being colonized on the microbial agent with biochar as the carrier and cultured to form the microbial agent so as to be rapidly propagated in the microenvironment provided by biochar and degrade TBBPA that is in water and absorbed by biochar.

Specifically, a homology comparison method of a strain Y17 gene sequence is as follows: an NCBI website is logged to upload Y17 strains for BLAST comparison, and other strains with a homology similar to that of this strain are selected. It is found that the strain Y17 and *Burkholderia cepacia* isolate 4 are in the same branch, and they have a similarity of up to 99.58%. Therefore, it is determined that the Y17 strain is the *Burkholderia cepacia* strain.

In this example, the Y17 strains are bred and domesticated by the following steps:

D1, primary domestication: TBBPA polluted soil samples containing terrestrial *Burkholderia cepacia* strains were collected, every 10 g of soil was one breeding sample, and then multiple breeding samples were prepared; each of the samples was placed in a 200 mL inorganic salt culture medium respectively to be cultured by shaking and then underwent standing, then 20 mL of inoculating solution was put into a new 180 mL inorganic salt culture solution containing 1 mg/L TBBPA to be cultured by shaking for 7 days, the above steps were repeated for 5 times so as to gradually increase the concentration of TBBPA to 20 mg/L, and the obtained culture solution was subjected to plate streaking on a solid culture medium containing 20 mg/L TBBPA to undergo inverted culture at 30° C. The growth of colonies after each sample was domesticated was observed. If *Burkholderia cepacia* strains were survived, step D2 started, and if no *Burkholderia cepacia* strains were survived, this sample was discarded.

D2, secondary domestication: samples in which *Burkholderia cepacia* strains were survived were secondarily domesticated, namely, single colonies were picked and inoculated to a 20 mL inorganic salt culture medium containing 1 mg/L TBBPA with the pH of 7±0.2 to be cultured for 7 days at 30° C. under 160 rpm/min. The residual quantity of TBBPA was determined, a culture solution of a sample without a removal effect was discarded, a culture solution of a sample with a removal effect was streaked on the solid culture medium again to be purified, and the growth of colonies of the samples after secondary domestication was observed.

D3, verification and optimization of biological characteristics: the growth of colonies of each sample after secondary domestication was respectively observed, the measured residual quantity data of TBBPA in each sample was compared, and then a survived *Burkholderia cepacia* strain which is the most strongest and meanwhile has minimal residual quantity of TBBPA was selected for isolation and extraction of strains, so as to obtain a domesticated single strain Y17 with strong TBBPA removal activity.

D4, the Y17 strains were rejuvenated and expanded using a nutrient culture medium before being used for degrading TBBPA in water, and the process was as follows: the strains were added into the nutrient culture medium, and then expanded for 12 at 35° C. under the rotation speed of 160 r/min; the nutrient culture medium was obtained by adding 3 g of beef extract, 10 g of peptone and 5 g of NaCl into pure water, fixing the volume to 1000 mL and adjusting the pH to 7.2.

The obtained solid culture medium was prepared by adding TBBPA as an only carbon source into the inorganic salt culture medium, making the final concentration of TBBPA be 20 mg/L, adding 17 g of agar in each liter and adjusting the pH to 7.2.

The inorganic salt culture medium was a solution obtained by adding 1.3 g of KCl, 0.2 g of $KH_2PO_4$, 1.17 g of NaCl, 0.1 g of $CaCl_2 \cdot H_2O$, 0.18 g of $MgCl_2 \cdot 6H_2O$, 1 mg/L of vitamin (wherein, 0.05 mg/L of vitamin B1, 0.05 mg/L of riboflavin, 0.10 mg/L of vitamin B6, 0.02 mg/L of vitamin H, 0.02 mg/L of folic acid, 0.1 mg/L of vitamin B12, 0.05 mg/L of niacin, 0.05 mg/L of lipoic acid and 0.05 mg/L of p-aminobenzoic acid) and 63.6 mg/L of trace elements (wherein 20 mg/L of $MnCl_2 \cdot 4H_2O$, 30 mg/L of $CoCl_2 \cdot 6H_2O$, 5.7 mg/L of $H_3BO_3$, 2.7 mg/L of $CuCl_2 \cdot 2H_2O$, 2.6 mg/L of $NaMoO_4 \cdot 2H_2O$, 2.1 mg/L of $ZnCl_2$ and 0.5 mg/L of $NiCl_2 \cdot 6H_2O$) into pure water, fixing the volume to 1000 mL and adjusting the pH to 7.2.

The microbial agent for degrading TBBPA in water provided in this example was prepared by adopting the following steps:

A, Preparation of Biochar BC biomass maize straws were dried in an oven at 60° C. and grinded via a 150 μm sieve, a certain amount of sieved biomass was put into a corundum boat to be placed in a tubular furnace, and the heating procedure of the tubular furnace was as follows: the room temperature was respectively raised to 300° C., 500° C. and 700° C. at 10° C./min for pyrolysis, the above pyrolysis temperatures were kept for 2 h, and each of the pyrolysis temperatures was reduced to 75° C. at 10° C./min, and then the biomass was taken out for future use, thereby obtaining three kinds of biochar BC corresponding to their pyrolysis temperatures, marking as BC300, BC500 and BC700; FIG. 1 is an SEM image of biochar material BC500. It can be seen from FIG. 1 that the BC500 has layered substances with different sizes and shapes which mutually form multiple pore channels (pores), thus has a large specific surface area, clean surface and no dust and impurities, and is suitable for growth of microorganisms adhered to the surface and the pore channels.

Refer to Table 1 and Table 2, in the preparation process of biochar, with the increase of temperature, the content of the C element in maize straws is increased from 40.45% to 56.51%, the content of the H element in maize straws is decreased from 5.82% to 1.82%, and the content of the O element in maize straws is decreased from 41.35% to 7.99%, indicating that the pyrolysis dehydrogenation and deoxygenation reactions occurred in the process of protoplast pyrolysis. The atomic ratio (N+O)/C of biochar reflects the polarity of biochar, H/C reflects the aromaticity of biochar, and O/C reflects the hydrophilicity of biochar. With the raising of the temperature, (N+O)/C, H/C and O/C ratios are all decreased. The aromaticity of biochar is enhanced, while the hydrophilicity and the polarity are decreased. With the raising of the temperature, the specific surface area, surface area and pore volume of biochar are all increased, but the pore channels may be blocked with the raising of the temperature and the increase of the ash content may block the pore channels. The zeta potential of biochar is negative, and the surface of biochar is negatively charged. With the raising of the temperature, the zeta potential is increased (see FIG. 4), and the reduced negative charge of biochar is conducive to the macroscopic adsorption of microorganisms.

TABLE 1

Particle size and pore structure characteristics of biochar

| Biochar | Specific surface area $m^2/g$ | Micropore area $m^2/g$ | Outer surface area $m^2/g$ | Pore volume $m^2/g$ |
|---|---|---|---|---|
| BC300 | 6.7181 | 0.0000 | 6.7181 | 0.0156 |
| BC500 | 11.8105 | 0.2323 | 11.5782 | 0.0225 |
| BC700 | 17.3158 | 3.7215 | 13.5943 | 0.0275 |

TABLE 2

Element compositions, atomic ratios and ash contents of biochar

| Biochar | Element compositions | | | | | Atomic ratio | | | Ash contents |
|---|---|---|---|---|---|---|---|---|---|
| | N % | C % | H % | S % | O % | (N + O)/C | H/C | O/C | |
| BC300 | 2.07 | 54.98 | 4.27 | 0.22 | 21.48 | 0.18 | 0.93 | 0.15 | 16.98 |
| BC500 | 1.79 | 54.64 | 2.59 | 0.25 | 13.32 | 0.12 | 0.57 | 0.09 | 27.41 |
| BC700 | 1.43 | 56.51 | 1.82 | 0.23 | 7.99 | 0.07 | 0.39 | 0.05 | 32.02 |

B, Preparation of microbial agent MBC by immobilized colonization of biochar

The biochar prepared under different pyrolysis conditions and an isolated and purified single strain Y17 solution with removal activity were used to undergo immobilized culture at the rotation speed of 169 r/min at the temperatures of 25° C., 30° C., 35° C. at the pH of 5, 6, 7, 8 and 9 to colonize the microorganisms onto the biochar so as to prepare the biochar immobilized microbial agent MBC, and then the obtained microbial agent MBC was rinsed with sulfate buffer for future use; according to the used carrier biochar, MBC300, MBC500 and MBC700 were respectively marked. The SEM in FIG. 2 shows that the microbial strain Y17 has been successfully immobilized (colonized) on the carrier of biochar.

A method for removing TBBPA in water comprises the following steps:

S1, the microbial strain Y17 capable of degrading TBBPA in water and the microbial agents MBC300, MBC500 and MBC700 were respectively prepared;

S2, the concentration of TBBPA in wastewater and the degradation rate of the prepared microbial agent were measured, and the amount of the microbial agent required for degradation was calculated;

S3, the microbial agents MBC300, MBC500 and MBC700 were respectively added into wastewater, wastewater was stirred or vibrated, or naturally flowed for 7-8 days so that the microbial strain Y17 on the microbial agent was continuously and aerobically grew, adsorbed and degraded TBBPA in wastewater: at this moment, the microenvironment for growth of Y17 strains was formed on the surface and pore channels of biochar, the dissolved oxygen in wastewater and the air reserved in the pore channels of biochar continuously provided oxygen sources to the degradation reaction process, the TBBPA adsorbed by biochar was used as a carbon source, the low osmotic pressure of wastewater was hedged on the combination surface of biochar and wastewater, and a high osmotic pressure was provided for Y17 strains; Y17 strains aerobically grew and are propagated in wastewater for bio-enhanced degradation of TBBPA in wastewater;

The first degradation process also included the steps of observing the degradation effect of MBC300, MBC500 and MBC700 under the same conditions; and adding the microbial agent with the best effect when the next addition;

S4, the concentration of TBBPA in treated wastewater was measured, steps S2-S3 were repeated if the concentration failed to meet the standard, until qualified.

The technical solution provided by this example focuses on screening and domesticating strain Y17, and then colonizing (immobilized culture) the above strain Y17 on the surface and pore channels of biochar to form the microbial agent which provides the growth conditions and microen-vironment for aerobic growth of Y17 strains in water to degrade TBBPA in water. It can be seen by observing FIG. 2-FIG. 3 that after the microbial agent (FIG. 2) in which biochar is used as the carrier is added into water, Y17 strains grow on the surface and pore channels of biochar, the biochar adsorbs TBBPA in water to serve as the carbon source for growth of Y17 strains, the air reserved in the pore channels of biochar and the dissolved oxygen in water are used as oxygen sources, the high osmotic pressure is provided on the contact surface between the biochar and water so that the degradation reaction can continuously conducted. After 12 hours, a small amount of Y17 strains (FIG. 2) undergo rapid growth and fission so as to be widely distributed on the surface and pore channels of biochar (FIG. 3). In the figure, the approximately elliptical or cylindrical parts are the Y17 strains which are naturally and unevenly distributed on the surface and pore channels of biochar.

According to the embodiments of the present disclosure, microscopic conditions conducive to the growth of Y17 strains in water are created through a special microbial agent to realize the enhanced degradation of pollutants. The strain is colonized onto the biochar carrier to prepare a special microbial agent which is easy for preparation, storage, sowing and use in batches.

Figure 10:
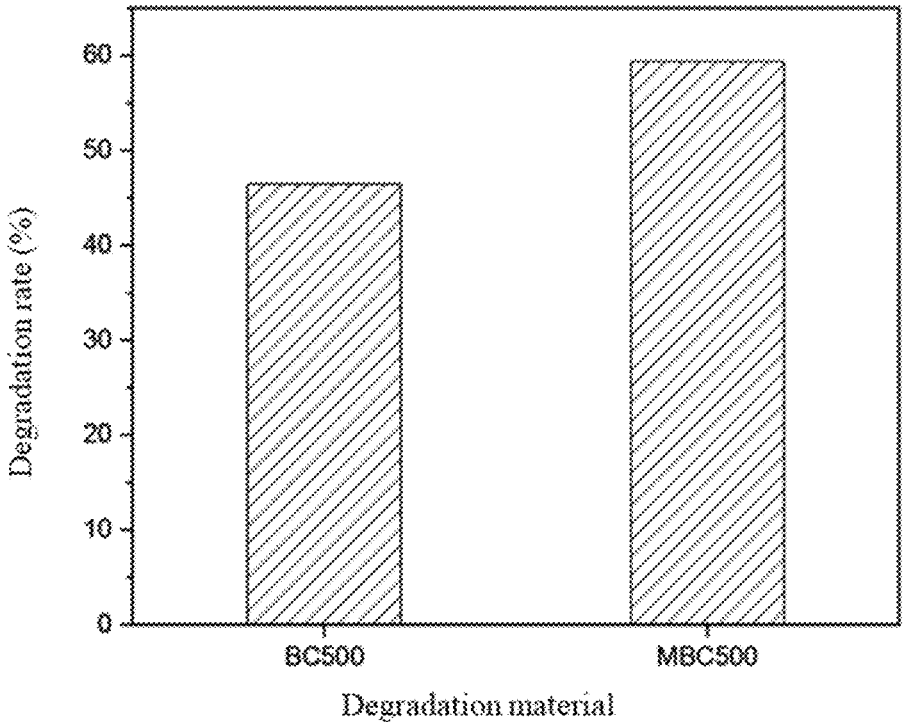
FIG. 10 is a diagram showing comparison between TBBPA removal efficiencies of traditional biochar and biochar in the present disclosure according to embodiments of the present disclosure.

Refer to FIG. 10, this example uses Y17 strains and the microbial agent MBC. It can be seen by comparing with the effect generated by using traditional biochar to remove TBBPA in water that under the same conditions, the removal efficiency of the microbial agent of the present disclosure is improved by about 30%.

Example 2

The method, microbial strain and microbial agent for degrading TBBPA in water provided by this example are basically the same as those in example 1. The difference is that the specific gravity of the microbial agent is adjusted by adjusting the preparation conditions of biochar, so that the microbial agent can suspend in water for a long time, thereby improving the degradation efficiency.

The step A of preparing the microbial agent for degrading TBBPA in water also comprises the following steps:

the biochar BC500 heated to 500° C. was added into a vibration screening machine, and forward and reverse alternating wetting pressure air was introduced into the vibration screening machine while vibration, ashes are removed, and the blocked pore channels are opened up so that the wet air is accommodated in each pore channel of biochar and the negative charges carried by biochar were reduced so as to facilitate the macroscopic adsorption of microorganisms and meanwhile the prepared biochar material had the following performance parameters: the initial specific gravity (dry weight) was 0.35-0.36, the specific surface area was 11.7-11.9 m²/g, the micropore area was 0.23-0.24 m²/g, the outer surface area was 11.4-11.6 m²/g, and the pore volume was 0.02-0.03 cm²/g;

the step B of preparing the microbial agent for degrading TBBPA in water also comprises: the biochar BC500 treated in step A was used as a carrier to undergo immobilization culture of biochar for 12 h at the immobilization culture temperature of 35° C. at the immobilization culture pH of 7 to prepare a suspension type microbial agent MBC 500.

Figure 4:
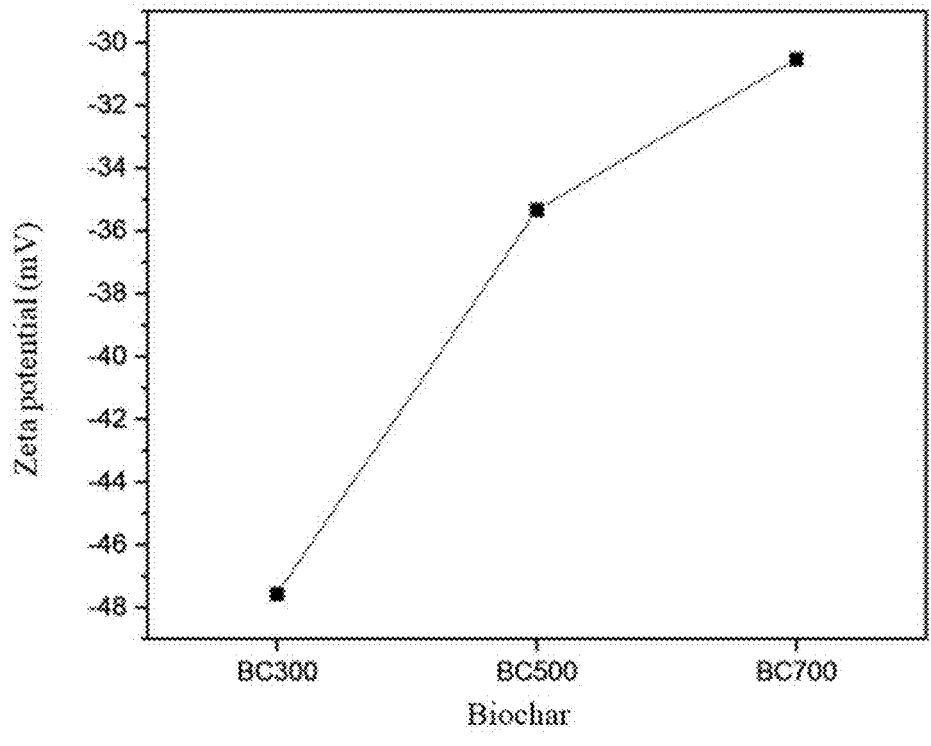
FIG. 4 is a Zeta potential diagram of a surface of biochar according to embodiments of the present disclosure.

Refer to FIG. 4, in step A, with the rising of the preparation temperature, the specific surface area, surface area and pore volume of biochar are gradually increased, but with the rising of the temperature and the increase of the ash content, the pore channels may be blocked, and meanwhile the specific gravity is reduced; the Zeta potential of biochar treated in this step is negative, the surface of the biochar is negatively charged, the reduction in negative charges carried by biochar are conducive to macroscopic adsorption of microorganisms along with the rising of the pyrolysis temperature and the increase of the Zeta potential. A practical test shows that the specific gravity, pore volume and other parameters of BC500 are preferably suitable for preparing the suspension type microbial agent MBC500.

The suspension type microbial agent MBC500 prepared by BC500 has the following performance parameters: the initial specific gravity is 0.35~0.36, the specific surface area is 11.7~11.9 m²/g, the micropore area is 0.23~0.24 m²/g, the surface area is 11.4~11.6 m²/g, the pore volume is 0.02-0.03 cm²/g; the specific gravity after sufficient immersion is 0.98-0.99 so that the Y17 strains suspend in water for a long time, and aerobically grow for a long time to continuously degrade TBBPA in water.

The method for removing TBBPA in water provided in this example comprises the following steps:

S1: preparing the microbial agent MBC500 of this example;

S2: measuring the concentration of TBBPA in wastewater and the degradation rate of the prepared microbial agent, and calculating the amount of the microbial agent required for degradation;

the step S3 is as follows the microbial agent MBC500 was added into wastewater, wastewater was stirred and vibrated, or naturally flew for 7-8 days. After sufficient immersion, the specific gravity of the microbial agent was 0.98-0.99, the microbial agent the Y17 strains suspended in water for a long time so that the Y17 strains aerobically grew for a long time so as to improve the adsorption and degradation efficiencies of TBBPA in water; and S4: measuring the concentration of TBBPA in the treated wastewater, and repeating steps S2-S3 if fail to meet the standard, until qualified.

The average specific gravity of the suspension type microbial agent MBC500 of this example after sufficiently absorbing water is close to 1 (specific gravity of water). Under natural conditions, most of microbial agent particles can suspend in water for a long time, and a small amount of microbial agents can be deposited on the surface of the sediment. The microbial agent creates a microenvironment (including environments where suspended strains bear a low water pressure). In this example, the specific gravity of the biochar microbial agent is adjusted by adjusting the preparation conditions of biochar. After fully absorbing water, water locally enters the pore channels of biochar, air is accommodated inside the biochar, the microbial agent can suspend in water and provides partial oxygen source for growth of the strains; biochar adsorbs TBBPA through its surface and pore structure, the Y17 strains grow and are propagated on the combination surface between biochar and water to improve the degradation speed and efficiency.

The MBC500 of this example suspends in water so that the microbial agent and the Y17 strains are in a shallow depth in water; at the same time, the air on the surface and pore channels of biochar also help hedging the low osmotic pressure in water and improving the high osmotic pressure of Y17, which is conducive to continuous and rapid degradation reaction.

Example 3

Figure 5:
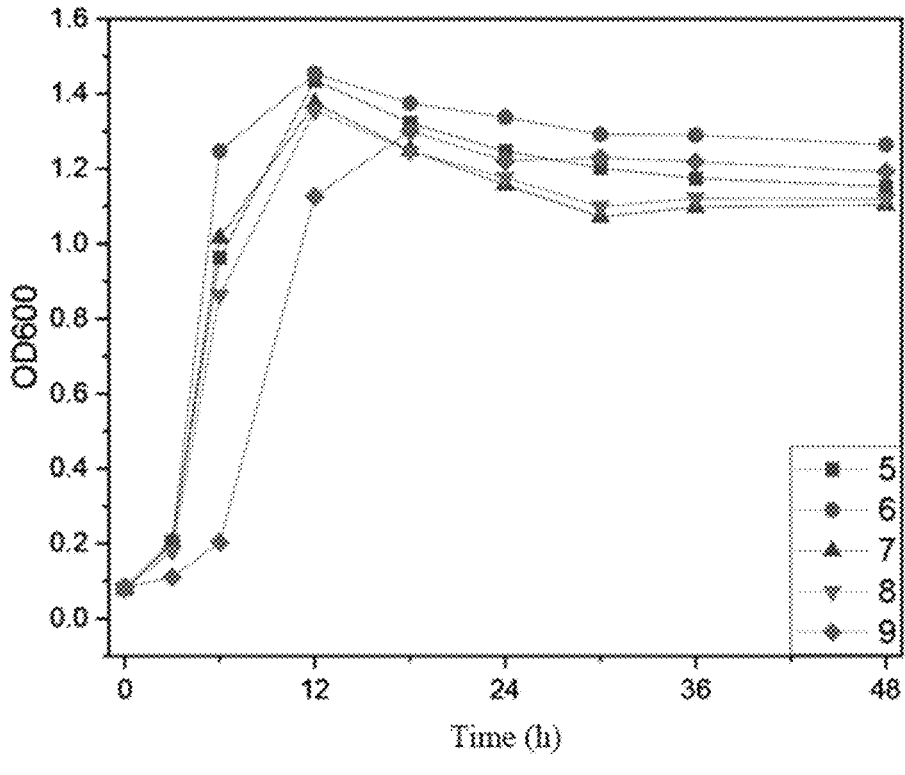
FIG. 5 is a diagram showing influence of pH on a growth curve of a microbial agent according to embodiments of the present disclosure.

Refer to FIG. 5, this example is a specific application of the technical solutions provided in examples 1 and 2, focusing on respectively testing the influence of different pH conditions of water on the performance of the domesticated Y17 strains to degrade TBBPA.

The test method is as follows: after being amplified to OD600 of 0.45, the Y17 strains were inoculated into the nutritional culture medium in a 5% inoculation amount, and the strains were cultured at a constant temperature in water containing TBBPA at the temperature of 35° C. under the rotation speed of 160 r/min at the pH of 5, 6, 7, 8 and 9 respectively; in 12 hours, the concentration of microorganisms basically reached a peak, and when pH was 6, the concentration of microorganisms was the highest. Its growth curve is as shown in FIG. 5.

Accordingly, the optimal growth pH value of the domesticated Y17 strains is 6. The environmental adaptability of Y17 strain is improved compared with that of the original strain.

Example 4

Figure 6:
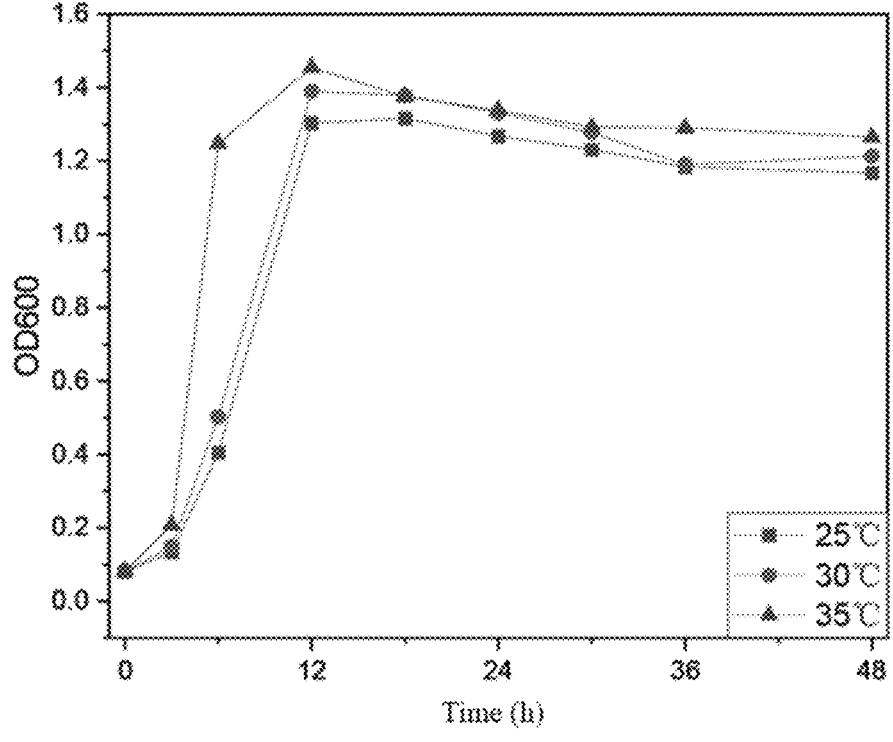
FIG. 6 is a diagram showing influence of a temperature on a growth curve of a microbial agent according to embodiments of the present disclosure.

Refer to FIG. 6, this example is a specific application of the technical solutions provided by examples 1 and 2, focusing on respectively testing the influence of different water temperature conditions on the performance of the domesticated Y17 strains to degrade TBBPA.

The test method is as follows: after being amplified to OD600 of 0.45, the Y17 strains were inoculated into the nutritional culture medium in a 5% inoculation amount, and the strains were cultured at constant temperatures of 25° C., 30° C. and 35° C. under the rotation speed of 160 r/min at the pH of 6; in 12 hours, the concentration of microorganisms reached a peak, and when the temperature was 35° C., the concentration of microorganisms was the highest, namely, when the temperature was 35° C. and the pH value was 6, the maximum value was reached after being cultured for 12 h.

It can be seen from a curve of temperature on microbial growth that the optimal biochar immobilized culture time is 12 h.

Example 5

Figure 7:
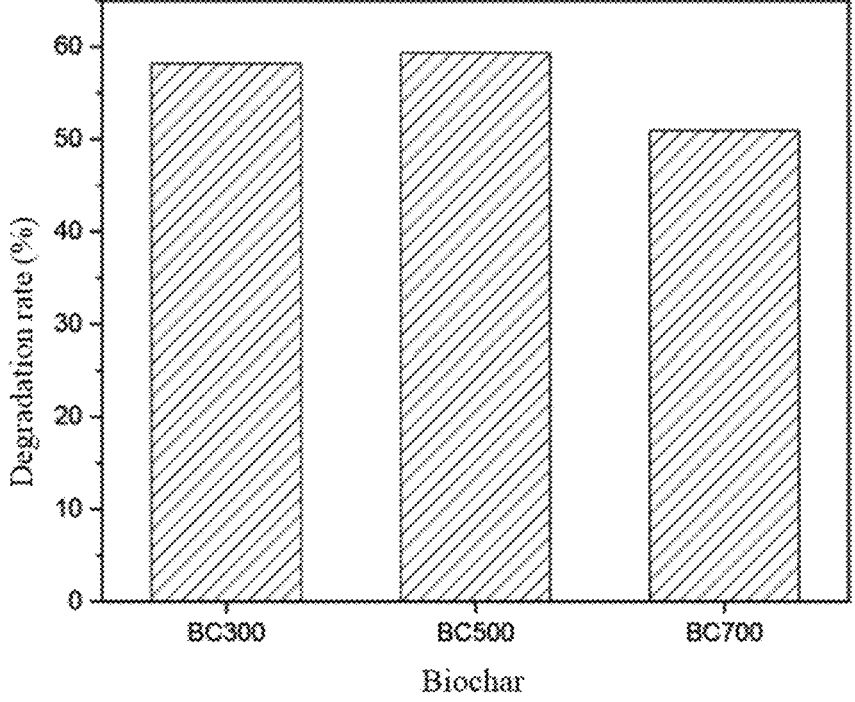
FIG. 7 is a diagram showing influence of different pyrolysis temperatures on the efficiency of a biochar immobilized colonizing microbial agent to degrade TBBPA according to embodiments of the present disclosure.

Refer to FIG. 7, this example is a specific application of the technical solutions provided in examples 1 and 2, focusing on testing the influence of various biochar BC prepared at different pyrolysis temperatures and further prepared microbial agent MBC on the performance of the Y17 strains to degrade TBBPA.

The test method is as follows: 5 mg of biochar immobilized colonizing microbial agent with an immobilized culture temperature of 35° C., an immobilized culture pH value of 7, and biochar preparation methods of 300° C., 500° C. and 700° C. respectively was added into a 50 mL inorganic salt medium containing 1 mg/l TBBPA, and then oscillated in a thermostatic oscillator for 7 days under the conditions of 30±0.5° C., 160 r/min and pH of 7±0.2. As shown in FIG. 7, the removal rates of TBBPA are 39.37%-59.37%, and the removal rate is the highest when biochar is prepared at 500° C.

According to the diagram showing the degradation efficiency of TBBPA by the biochar immobilized colonizing microbial agent at different pyrolysis temperatures as shown in FIG. 7, it can be seen that the optimal pyrolysis preparation temperature of biochar is 500° C.

Example 6

Figure 8:
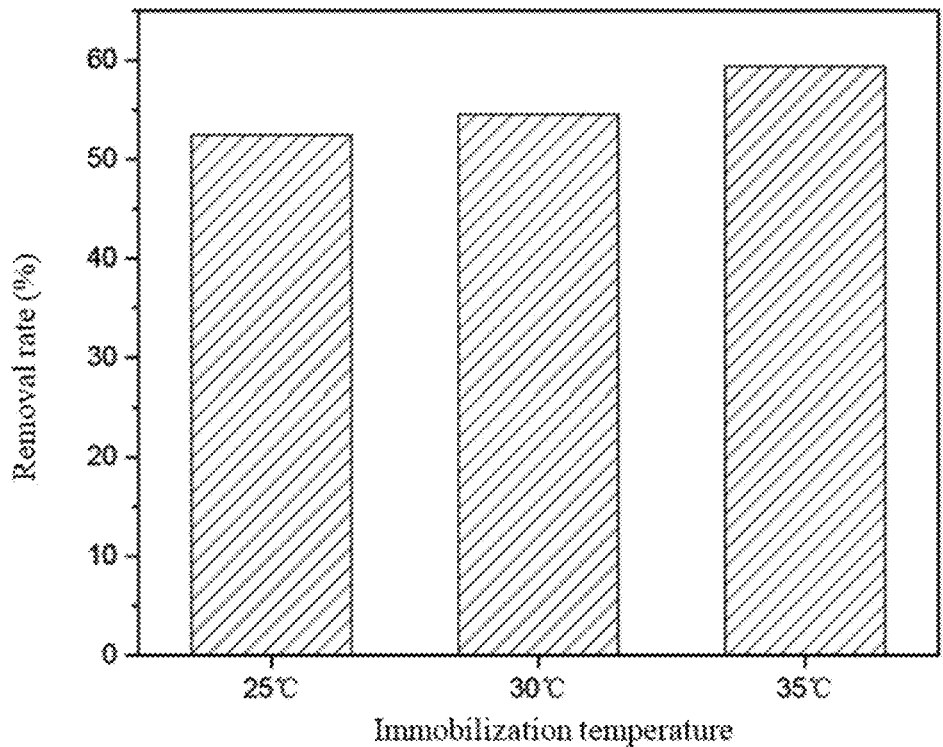
FIG. 8 is a diagram showing influence of different immobilization culture temperatures on the efficiency of a biochar immobilized colonizing microbial agent to degrade TBBPA according to embodiments of the present disclosure.

Refer to FIG. 8. This example is a specific application of the technical scheme provided by examples 1 and 2, focusing on testing the influence of microbial agents MBC prepared at different immobilization temperatures on the performance of adsorbing and degrading TBBPA.

The test method: is as follows: 5 mg of biochar immobilized colonizing microbial agent with immobilized culture temperatures of 25° C., 30° C. and 35° C., an immobilized culture pH value of 7, and a biochar preparation method of 500° C. respectively was added into a 50 mL inorganic salt medium containing 1 mg/l TBBPA, and then oscillated in a thermostatic oscillator for 7 days under the conditions of 30±0.5° C., 160 r/min and pH of 7±0.2. The removal rates of TBBPA are 52.49%-59.37%, and the removal rate is the highest when the immobilized culture temperature is 500° C.

According to the influence of different immobilized culture temperatures on the efficiency of the biochar immobilized colonizing microbial agent to degrade TBBPA as shown in FIG. 8, it can be seen that the optimal immobilized culture temperature for preparing the microbial agent is 35° C.

Example 7

Figure 9:
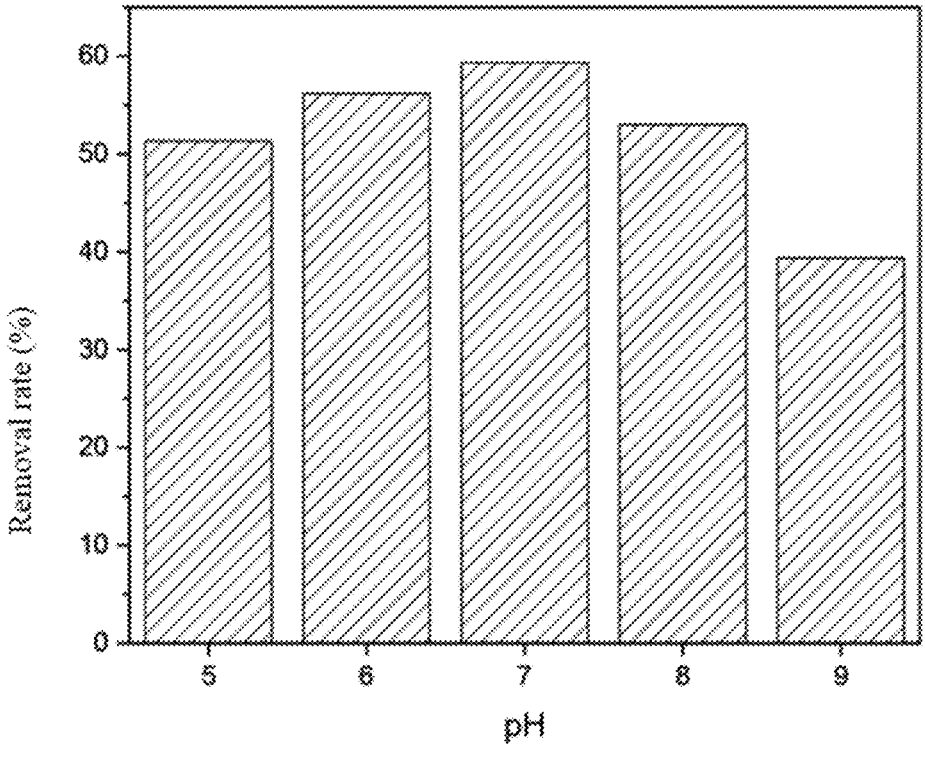
FIG. 9 is a diagram showing influence of different immobilization culture pH values on the efficiency of a biochar immobilized colonizing microbial agent to degrade TBBPA according to embodiments of the present disclosure.

Refer to FIG. 9, this example is a specific application of the technical solutions provided by examples 1 and 2, testing the influence of microbial agents MBC prepared at different immobilization temperatures on the performance of adsorbing and degrading TBBPA.

The test method is as follows: 5 mg of biochar immobilized colonizing microbial agent with an immobilized culture temperature of 35° C., an immobilized culture pH values of 5, 6, 7, 8 and 9 and a biochar preparation method of 500° C. respectively was added into a 50 mL inorganic salt medium containing 1 mg/l TBBPA, and then oscillated in a thermostatic oscillator for 7 days under the conditions of 30±0.5° C., 160 r/min and pH of 7±0.2.

As shown in FIG. 9, the TBBPA removal rate of the biochar immobilized colonizing microbial agent is 50.89%-59.37%, and the optimal immobilized culture pH value is 7.

Example 8

This example is a specific application of the technical solutions provided in examples 1 and 2, focusing on the comparison between the performances of untreated (excluding Y17) biochar BC and the microbial agent MBC for the degradation of TBBPA.

The test method is as follows: 50 mg of microbial agent Y17, 5 mg of biochar immobilized colonizing microbial agent with a biochar preparation method of 500° C., an immobilized culture temperature of 35° C. and an immobilized culture pH value of 7 and a biochar material with a preparation method of 500° C. were added into a 50 mL inorganic salt culture medium containing 1 mg/L TBBPA, and then oscillated in a thermostatic oscillator for 7 days under the conditions of 30±0.5° C., 160 r/min and pH of 7±0.2, as shown in FIG. 10, compared with the biochar material, the removal rate of the biochar immobilized colonizing microbial agent is improved by 12.94% and is 59.37%; accordingly, by comparing the microbial agent MBC containing Y17 with the biochar BC without Y17, the efficiency and effect of degrading TBBPA are improved by about 30%.

Example 9

This example is a specific application of the technical solutions provided in examples 1 and 2, focusing on comparison test of TBBPA removal effect data verified by the engineering practice and TBBPA removal effect data obtained in a laboratory to determine the actual degradation efficiency and effect of the microbial agent under natural conditions (affected by the environment).

Comparison test method: 1000 cubic meters of wastewater containing TBBPA to be treated were stored in reservoir A of a factory, 1 cubic meter of wastewater was retrieved and put into laboratory container B; the microbial agent MBC500 prepared in this example was added into the wastewater in the reservoir A and the laboratory container B respectively according to the same mass ratio; according to the same speed, the wastewater in the reservoir A and the laboratory container B was stirred and continuously treated for 7 days, then the reduction in the contents of TBBPA in the reservoir A and the laboratory container B was tested. Through the actual test, it is found that the degradation rate of the microbial agent MBC500 on TBBPA in wastewater from the reservoir A under natural conditions is 43.59%, which is lower than that in laboratory container B by only 15.78%. It can be seen that the microbial agent MBC500 of the present disclosure has good environmental adaptability and small comprehensive environmental condition influence.

By breeding the dominant strain Y17 originating from the soil, the Y17 strain can be used as an microorganism for degrading TBBPA in water after being domesticated; after being domesticated, the environmental adaptability, TBBPA degrading ability and stress resistance of the strain are all significantly improved. To grow the Y17 strain in water, the strain is colonized on the biochar to prepare a special microbial agent, and then the microenvironment wherein the strain can grow in water is created by the microbial agent; through continuous aerobic growth and propagation of Y17, TBBPA in water is continuously degraded; the optimal preparation and environment conditions of the microbial agent in the process of aerobic degradation are further obtained to enhance the degradation effect and shorten the degradation time.

While improving the effect of removing TBBPA in water, the present disclosure is also committed to reducing the total amount and sowing times of a material system, improving the adaptability of strains and microbial agents to water environments to greatly reduce the cost of wastewater treatment and facilitate large-scale promotion. After practical testing, the effective removal of TBBPA in water can be realized by once sowing and degradation of 7-8 days to reach a set standard; by comparing the total water treatment solution with the traditional technology, the total cost can be saved by 70% or more, and the degradation efficiency can be improved by 30% or more.

It should be noted that, in other embodiments of the present disclosure, other different solutions obtained through specific selection within the scope of steps, components, proportioning and process parameters described in the present disclosure can achieve the technical effects described in the present disclosure, and therefore cannot be listed one by one herein.

The above descriptions are only preferred embodiments of the present disclosure, but do not limit the present disclosure in any forms. Without departing from the scope of the technical solution of the present disclosure, many possible variations and modifications can be made to the methods and technical contents disclosed above, or the methods and technical contents disclosed above can be modified as equivalent embodiments with equivalent changes. Any equivalent changes made according to components, proportioning and processes of the present disclosure should be included within the protective scope of the present disclosure.

What is claimed is:

1. A microbial strain for degrading tetrabromobisphenol A (TBBPA) in water, wherein the strain is a domesticated *Burkholderia cepacia* strain which is named Y17 with a conservation number GDMCC No. 62153 and a conservation date of Dec. 21, 2021, wherein the Y17 strain is obtained by a domestication process comprising the steps of:

D1, primary domestication: TBBPA-polluted soil samples containing terrestrial *Burkholderia cepacia* strains are collected; multiple breeding samples of 10 g soil each are prepared; each sample is placed in 200 mL of inorganic salt culture medium and cultured by shaking and standing; then 20 mL of inoculum is transferred to a new 180 mL inorganic salt culture solution containing 1 mg/L TBBPA and cultured by shaking for 7 days; this process is repeated 5 times to gradually increase the TBBPA concentration to 20 mg/L; the culture solution is then subjected to plate streaking on a solid culture medium containing 20 mg/L TBBPA for inverted culture at 30° C.; colony growth is observed after domestication; if *Burkholderia cepacia* strains survive, the process proceeds to step D2; if no *Burkholderia cepacia* strains survive, the sample is discarded;

D2, secondary domestication: single colonies are picked from samples that survived step D1 and inoculated into 20 mL of inorganic salt culture medium containing 1 mg/L TBBPA at pH 7±0.2, and cultured at 30° C. and 160 rpm for 7 days; the residual quantity of TBBPA is determined; culture solutions without a removal effect are discarded; culture solutions with a removal effect are streaked on the solid culture medium for purification; colony growth after secondary domestication is observed; and D3, verification and optimization: colony growth of each sample after secondary domestication is observed; the measured residual quantity data of TBBPA is compared; and the strongest surviving *Burkholderia cepacia* strain with minimal residual quantity of TBBPA is selected for isolation and extraction to obtain the domesticated single strain Y17 with strong TBBPA removal activity.

\* \* \* \* \*